United States Patent [19]
Laber et al.

[11] 3,982,007
[45] Sept. 21, 1976

[54] SYNERGISTIC COMPOSITIONS
[75] Inventors: Georg Laber; Eberhard Schutze, both of Vienna, Austria
[73] Assignee: Sandoz Ltd., Basel, Switzerland
[22] Filed: Feb. 6, 1975
[21] Appl. No.: 547,545

Related U.S. Application Data
[63] Continuation-in-part of Ser. No. 386,847, Aug. 8, 1973, abandoned.

[30] Foreign Application Priority Data
Aug. 14, 1972 Switzerland.................. 12008/72

[52] U.S. Cl................................. 424/270; 424/285
[51] Int. Cl.$^2$..................................... A61K 31/425
[58] Field of Search........................... 424/270, 285

[56] References Cited
OTHER PUBLICATIONS
Chemical Abstracts 63:2149(d) (1965).
Chemical Abstracts 66:1364(a) (1967).

Primary Examiner—Jerome D. Goldberg
Assistant Examiner—Allen J. Robinson
Attorney, Agent, or Firm—Gerald D. Sharkin; Robert S. Honor

[57] ABSTRACT
The invention provides synergistic compositions comprising a benzisothiazolinone derivative and a 2-nitrofuryl or 2-nitrothienyl derivative. The compositions are useful as antimicrobial agents.

7 Claims, No Drawings

SYNERGISTIC COMPOSITIONS

This application is a continuation in part of our copending application Ser. No. 386,847 filed Aug. 8, 1973 now abandoned.

The present invention relates to pharmaceutical compositions.

More particularly, the present invention provides a composition comprising a compound of formula I,

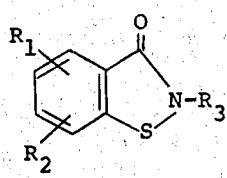   I in which
R₁ and R₂ are the same or different and each signifies hydrogen, lower alkyl, lower alkoxy, nitro, amino, carboxylic acid amide or halogen, and
R₃ is hydrogen, aminoalkyl, dialkylaminoalkyl, hydroxyalkyl, alkoxyalkyl, cycloalkyl, benzyl or phenylethyl, provided that at least one of R₁, R₂ and R₃ is other than hydrogen,
and a compound of formula II,

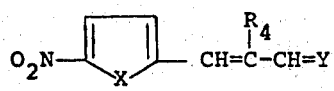   II in which
X is oxygen or sulphur,
R₄ is hydrogen, phenyl, or phenyl mono-, di- or tri-substituted by chlorine, bromine, fluorine, iodine, trifluoromethyl, hydroxy, nitro, benzyloxy, amino, lower alkyl, lower alkoxy, a lower alkylthio, or by -NHR₇,

-COOR₇, -CONH₂, -CONHR₇,

OCH₂CH₂OH or

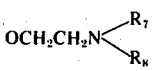

in which either R₇ and R₈ are the same or different and each signifies unsubstituted or substituted lower alkyl or phenyl, or R₇ and R₈ together with the nitrogen atom to which they are attached signify a 5- or 6-membered heterocycle which may contain one or more further hetero atoms selected from oxygen, sulphur and nitrogen, and which is unsubstituted or substituted, and Y is oxygen, or

in which Z is sulphur or =NH, the compound of formula I being present in an amount of from 10 to 90%, and the compound of formula II in an amount of from 90 to 10%, based on the total weight of the compounds I and II.

As used herein, "alkyl" or "alkoxy" when present as a substituent or part of a substituent, is preferably lower alkyl or alkoxy. Preferred such lower radicals contain 1 to 6, in particular 1 to 4, carbon atoms. "Halogen" is preferably chlorine or bromine. When a radical is substituted, unless otherwise indicated, it is preferably substituted by alkyl of 1 to 4 carbon atoms, which may be substituted by chlorine, bromine, fluorine or hydroxy. Polysubstituted radicals, may, for example, be mono-, di- or tri-substituted. Cycloalkyl radicals preferably contain 5 to 8, in particular 5 or 6 ring carbon atoms.

The compounds of formula I are known and exhibit a growth-inhibiting or destructive effect towards a wide spectrum of microorganism, such as bacteria, fungi and protozoa, in particular Staph. aureus, E. coli or Proteus vulgaris. They are therefore indicated for use as locally effective antimicrobial agents and are also suitable for topical use, e.g. in the form of ointments, powders for strewing or tinctures.

The compounds of formula II are either known or may be produced in conventional manner from available materials, for example as described hereinafter and illustrated in the Examples. These compounds also have antibacterial activity similar to that described in the literature for 2-nitrofuryl and 2-nitrothienyl derivatives.

The present invention is based on the finding that the combination of the compounds I and II exhibits an effect which is surprisingly considerably superior to the sum of the effects of the individual components.

Suitable compounds of formula I include those in which R₂ is hydrogen, particularly those of formula Ia,

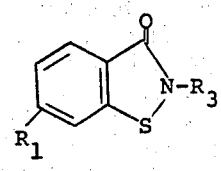   Ia in which R₁ and R₃ are as defined above, more particularly those of formula Ib,

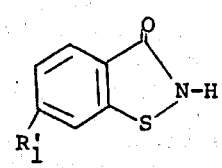   Ib in which R₁' has the same significance as R₁, defined above, except that it may not be hydrogen.

$R_1$ and $R_1'$ suitably signify halogen, lower alkyl, lower alkoxy, nitro or amino, more suitably halogen, lower alkyl or lower alkoxy, particularly halogen.

As will be appreciated, the compounds of formula II encompass the following sub-classes of formulae IIa, IIb, and IIc,

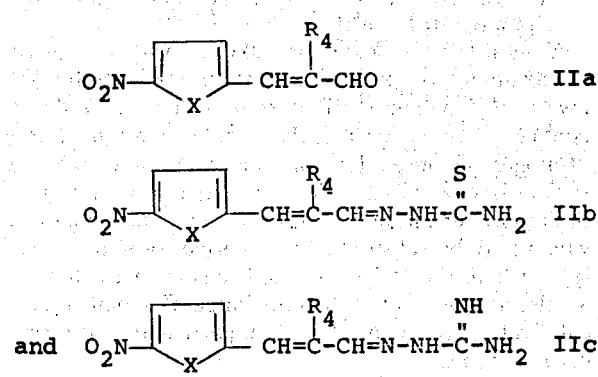

in which X and $R_4$ are as defined above.

The preferred compounds are those of formula IIc.

As indicated, X is either oxygen or sulphur, but is preferably oxygen. $R_4$ is preferably phenyl or monosubstituted phenyl. More preferably, $R_4$ is phenyl or phenyl monosubstituted by chlorine, bromine, nitro or benzyloxy, more particularly by chlorine or bromine.

The most preferred compounds of formula II are those of Examples 20, 21 and 22 hereinafter.

The compounds of formula I and the compounds of formula II in which

Y is =N—NH—C—NH$_2$, may be employed in free base form or in the form of pharmaceutically acceptable acid addition salts. Suitable such acid addition salts include organic acid salts, such as the fumarate, tartrate, or benzenesulphonate, and mineral acid salts, such as the hydrochloride, hydrobromide or sulphate.

The compositions of the invention preferably comprise the compound of formula I in an amount of from 20 to 35%, in particular about 25%, and the compound of formula II in an amount of from 80 to 65%, in particular about 75%, the percentages being based on the total weight of the compounds I and II.

As mentioned, the combination of the compounds I and II, exhibits an effect surprisingly superior to the sum of the effect of the individual components. This may be shown in conventional manner. For example, the minimum inhibiting concentration of each of the separate components may routinely be determined by using the series dilution test. The minimum inhibiting concentration of each component may then be redetermined in the presence of various concentrations of the other component. The results may then be treated graphically in accordance with Löwe's method (isobol diagram), Die Antibiotika, 1(1), 65- [1962].

The composition of the invention may be formulated in conventional manner and may include conventional inorganic or organic, pharmaceutically acceptable diluents or carriers, and, optionally, other excipients, and may also include other pharmacologically active adjuvants not materially adversely affecting the effect of the main active agents. The compositions may suitably be administered in such forms as tablets, capsules, powders, granulates, solutions or suspensions.

Inert adjuvants or additives which may be admixed with the compositions include sweetening agents, flavouring, colouring and preserving agents, fillers and carrier materials, for example diluents such as calcium carbonate, sodium carbonate, lactose, polyvinyl pyrrolidone, mannitol or talc, granulating and disintegrating agents such as starch or alginic acid, binding agents such as starch, gelatin or acacia, and lubricants such as magnesium stearate, stearic acid or talc. Preparations for oral administration may contain the usual suspending agents, e.g. methyl cellulose, tragacanth or sodium alginate. Examples of suitable wetting agents which may be used are: lecithin, polyoxyethylene stearate or polyoxyethylene sorbitan monooleate. Ethyl-o-hydroxybenzoate may, for example, be used as preserving agent. Examples of diluents which may be used in solid compositions, e.g. for the production of capsules are: calcium carbonate, calcium phosphate and kaolin.

The compositions of the invention are indicated for use in the treatment of microorganism infections in humans and in domestic animals, e.g. pigs or calves, in particular in infections of the gastrointestinal tract and other local infections in the organism. For such use, the dosage administered will, of course, vary depending on the composition, mode of administration and treatment desired. However, in general, satisfactory results are obtained when administered at a daily dosage of from about 100 to 500 mg/kg of animal body weight, conveniently given as a single dose or in divided doses two to five times daily. For the larger mammals, the total daily dosage is from about 3 to 15 g and dosage forms suitable for oral administration comprise from about 600 mg to 7.5 g of the composition admixed with a solid or liquid pharmaceutical diluent or carrier.

In the case of treatment of domestic animals, the compositions may suitably be administered with feedstuff or drinking water. The dosage will of course vary depending on the size and age of the animal and the effect desired. An indicated suitable unit dose for calves is from about 4 to 6 g and for young to medium pigs, from about 500 mg to 5 g. Such unit doses may suitably be administered 1 to 3 times daily.

The compounds of formula II may be produced, for example, as follows:

1. A compound of formula IIa, stated above, may be obtained by reacting a compound of formula III,

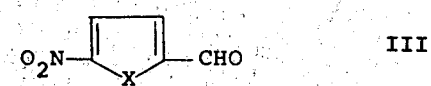

or of formula IIIa,

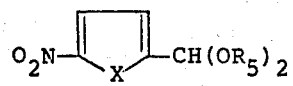

wherein X is as defined above, and $R_5$ is lower alkyl, with a compound of formula IV,

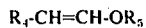

wherein $R_4$ and $R_5$ are as defined above, or, where a compound of formula III is employed, with a compound of formula IVa,

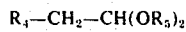

wherein $R_4$ and $R_5$ are as defined above, in the presence of a Friedel-Crafts catalyst, and hydrolysing the resulting complex.

The process may, for example, be effected by dissolving a compound of formula III or IIIa in an inert solvent, e.g. an aromatic hydrocarbon such as benzene, then adding the catalyst, e.g. diethyl ether, trifluoroborane or zinc chloride, and subsequently adding dropwise a compound of formula IV or IVa whereby the reaction temperature is preferably kept at 0°C to room temperature. For the acceleration and completion of the reaction heating may subsequently be effected, e.g. to 30° to 50°C. After the reaction is complete, the resulting reaction complex is hydrolysed using an acid, e.g. by the addition of aqueous hydrochloric acid.

2. A compound of formula IId,

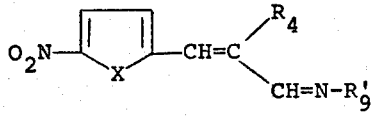

wherein X and $R_4$ are as defined above, and $R_9'$ is

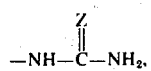

in which Z is as defined above, may be obtained by reacting a compound of formula IIa, stated above, with a compound of formula V,

wherein $R_9'$ is as defined above.

The process may, for example, be effected by adding a compound of formula V to a solution of a compound of formula IIa in an inert solvent, e.g. a lower alcohol such as ethanol or methanol, and heating to a high temperature, preferably to 50°C to the boiling temperature of the reaction mixture. A catalyst, e.g. sodium acetate, may optionally be added.

The starting materials of formulae III, IIIa, IV, IVa and V are known or may be produced in accordance with known processes or in a manner analogous to known processes.

In the following non-limitative Examples, all temperatures are indicated in degrees Centigrade.

Examples for the production of the compounds of formula II

EXAMPLE 1

2-(2-chlorophenyl)-3-(5-nitro-2-furyl)acrolein 4.0 g of 1-(2-chlorophenyl)-2-methoxyethylene are added dropwise within 20 minutes to 9.55 g of 5-nitrofurfurol in 12 cc of dry benzene at room temperature after the addition of one drop of diethyl ether/trifluoroborane. The mixture is stirred at 35°–40° for 1 hour and is then successively washed with a 5% aqueous sodium acetate solution and water, the benzene solution is dried over magnesium sulphate and concentrated by evaporation. The residue is taken up in 3 cc of concentrated hydrochloric acid, 17 cc of water and 120 cc of glacial acetic acid, and the mixture is stirred at 80°–85° for 3 hours. The mixture is concentrated in a vacuum, and, after cooling, the title compound is obtained as yellow crystals having a M.P. of 148°–151°.

The following 2-nitrofuryl derivatives of formula IIId may also be obtained in a manner analogous to that described in Example 1 (Examples 2 to 8):

EXAMPLE 2

2-(4-bromophenyl)-3-(5-nitro-2-furyl)acrolein
M.P. 148°–151°.

EXAMPLE 3

3-(5-nitro-2-furyl)-2-phenylacrolein
M.P. 106°–109°.

EXAMPLE 4

2-(4-chlorophenyl)-3-(5-nitro-2-furyl)acrolein

EXAMPLE 5

2-(2-bromophenyl)-3-(5-nitro-2-furyl)acrolein
M.P. 127°–132°.

EXAMPLE 6

2-(3-bromophenyl)-3-(5-nitro-2-furyl)acrolein
M.P. 156°–160°.

EXAMPLE 7

3-(5-nitro-2-furyl)-2-(2-nitrophenyl)acrolein
M.P. 160°–165°.

EXAMPLE 8

3-(5-nitro-2-furyl)-2-(4-nitrophenyl)acrolein
M.P. 185°–190°.

EXAMPLE 9

2-(4-nitrophenyl)-3-(5-nitro-2-thienyl)acrolein 3.04 g of 1-methoxy-2-(4-nitrophenyl)ethylene, diluted with 5 cc of benzene, are added dropwise at 0°–5° within 40 minutes to 0.8 g of 5-nitrothiophene-2-aldehyde in 20 cc of dry benzene after the addition of a few drops of diethyl ether/trifluoroborane. The mixture is stirred at 40° for 1 hour, is successively washed with a 5% aqueous sodium acetate solution and with water, is dried with magnesium sulphate and concentrated by evaporation. 20 cc of 10% hydrochloric acid and the necessary amount of glacial acetic acid to form a homogeneous solution at 90° for 4 hours. The residue obtained after concentration is taken up in chloroform, the undissolved portion is filtered off and concentration by evaporation is effected, whereby the title compound is obtained in the form of brown crystals having a M.P. of 190°–192° (decomp.).

The following compounds of formula IIId may also be obtained in a manner analogous to that described in Example 9 (Examples 10 to 12):

EXAMPLE 10

2-(4-chlorophenyl)-3-(5-nitro-2-thienyl)acrolein 1-(4-chlorophenyl)-2-methoxyethylene is reacted in analogous manner with 5-nitrothiophene-2-aldehyde, and the title compound is obtained in the form of brown crystals having a M.P. of 135°–136°, after purification by column chromatography over silica gel with toluene.

EXAMPLE 11

2-(4-bromophenyl)-3-(5-nitro-2-thienyl)acrolein 1-(4-bromophenyl)-2-methoxyethylene is reacted in analogous manner with 5-nitrophene-2-aldehyde, and the title compound is obtained in the form of brown crystals having a M.P. of 105°–108° after purification by column chromatography over silica gel with toluene.

EXAMPLE 12

3-(5-nitro-2-thienyl)-2-phenylacrolein

β-methoxystyrene is reacted in analogous manner with 5-nitrophene-2-aldehyde, and the title compound is obtained after purification by column chromatography over silica gel with benzene/carbon tetrachloride (90:10).

EXAMPLE 13

2-(4-bromophenyl)-3-(5-nitro-2-furyl)acrolein-thiosemicarbazone 1.0 g of 2-(4-bromophenyl)-3-(5-nitro-2-furyl) acrolein and 0.31 g of thiosemicarbazide are heated at reflux for 30 minutes in 25 cc of methanol with 0.3 g of glacial acetic acid and 1.0 g of sodium acetate. Upon cooling, the title compound is obtained as yellow brown crystals having a M.P. of 230°–237°.

The following compounds may be obtained in a manner analogous to that described in Example 13 (Examples 14 to 18):

EXAMPLE 14

2-(2-chlorophenyl)-3-(5-nitro-2-furyl)acrolein-thiosemicarbazone

Brown crystals, M.P. 230° (decomp.).

EXAMPLE 15

2-(4-chlorophenyl)-3-(5-nitro-2-furyl)acrolein-thiosemicarbazone

Brown crystals, M.P. 240° (decomp.).

EXAMPLE 16

2-(2-bromophenyl)-3-(5-nitro-2-furyl)acrolein-thiosemicarbazone

Brown needles, M.P. 180° (decomp.).

EXAMPLE 17

2-(4-bromophenyl)-3-(5-nitro-2-thienyl)acrolein-thiosemicarbazone

Orange yellow crystals, M.P. 230° (decomp.).

EXAMPLE 18

2-(4-chlorophenyl)-3-(5-nitro-2-thienyl)acrolein-thiosemicarbazone

M.P. 240° (decomp.).

EXAMPLE 19

2-(4-chlorophenyl)-3-(5-nitro-2-thienyl)acrolein-guanylhydrazone

A solution of 0.46 g of aminoguanidine hydrogen carbonate in 5 cc of 10% hydrochloric acid is added to 1.0 g of 2-(4-chlorophenyl)-3-(5-nitro-2-thienyl)acrolein in 20 cc of methanol, and the mixture is heated to 50° for one hour. Upon cooling, the hydrochloride of the title compound is obtained as yellow crystals having a M.P. of 225°–227°.

The following compounds may be produced in a manner analogous to that described in Example 19 (Examples 20 to 25):

EXAMPLE 20

2-(2-chlorophenyl)-3-(5-nitro-2-furyl)acrolein-quanylhadrazone

Yellow crystals, M.P. of the hydrochloride 175° (decomp.).

EXAMPLE 21

2-(4-bromophenyl)-3-(5-nitro-2-furyl)acrolein-guanylhadrazone

Orange red crystals, M.P. of the hydrochloride 260° (decomp.).

EXAMPLE 22

2-(4-chlorophenyl)-3-(5-nitro-2-furyl)acrolein-guanylhydrazone

Orange yellow crystals, M.P. of the hydrochloride 250° (decomp.).

EXAMPLE 23

3-(5-nitro-2-furyl)-2-phenylacrolein-guanylhydrazone

Yellow crystals, M.P. of the hydrochloride 220° (decomp.).

EXAMPLE 24

3-(5-nitro-2-thienyl)-2-phenylacrolein-guanylhydrazone

Brown crystals, M.P. of the hydrochloride 265° (decomp.).

EXAMPLE 25

2-(4-bromophenyl)-3-(5-nitro-2-thienyl)acrolein-quanylhydrazone

Yellow brown crystals, M.P. of the hydrochloride 245°–250° (decomp.).

EXAMPLE 26

2-(4-benzyloxyphenyl)-3-(5-nitro-2-furyl)acrolein 6.4 g of 1-(4-benzyloxyphenyl)-2-methoxyethylene, diluted with 10 cc of benzene, are added dropwise at 0°–5° to 11.15 g of 5-nitrofuran-2-aldehyde in 30 cc of dry benzene after the addition of a few drops of diethyl ether/trifluoroborane. The mixture is stirred at 40° for 1½ hours, is washed with a 5% aqueous sodium acetate solution and with water, dried with magnesium sulphate and concentrated by evaporation. The residue is heated to 90° for 4 hours with 10% hydrochloric acid and glacial acetic acid. The mixture is again concentrated by evaporation, is taken up in ether and the acid salt portion is filtered off. After concentration, orange crystals having a M.P. of 145°–155°, crystallize from the ether solution.

Examples for the production of galenical preparations.

EXAMPLE 27

Production of an active agent granulate by spray drying

Composition of the starting mixture:

| | |
|---|---|
| 6-chlorobenzisothiazolinone | 60 g |
| 2-(2-chlorophenyl)-3-(5-nitro-2-furyl) acrolein-guanyl hydrazone | 180 g |
| bismuth subcarbonate | 1200 g |
| polyvinyl pyrrolidone | 120 g |
| mannitol | 1437 g |
| trisodium citrate (5½ H$_2$O) | 3 g |
| total amount | 3000 g |

The mannitol and the trisodium citrate are dissolved in 4 liters of water, and the solution is heated to 50°. The remaining components are then weighed, thoroughly mixed together and gradually added to the above solution. The resulting mixture is then homogenized in a homogenizer. If necessary, a further amount of water up to a total amount of 7 liters is added during homogenization, whereby subsequently 500 cc of water are used to rinse out the homogenizer. The resulting homogenized material is then spray-dried in the usual manner under a pressure of 4 atmospheres, whereby the temperature of admission amounts to 170° and the temperature of discharge to 85°–90°. The resulting spraydried preparation is moistened with 50% ethanol, pressed through a sieve DIN No. 7 and dried in a drying chamber at 43°.

EXAMPLE 28

Production of an active agent granulate by spray granulation

| Composition of the mixture: | |
|---|---|
| trisodium citrate | 30 g |
| water | 300 cc |
| bismuth subcarbonate | 6000 g |
| polyvinyl pyrrolidone | 600 g |
| water | 3000 cc |
| 6-chlorobenzisothiazolinone | 300 g |
| 2-(2-chlorophenyl)-3-(5-nitro-2-furyl) acrolein-guanyl hydrazone | 900 g |
| mannitol | 7170 g |
| total amount | 15000 g dry substance |

The trisodium citrate is first dissolved in 300 cc of water, whereupon the bismuth subcarbonate is placed in the bucket of the spray granulator and is sprayed with the sodium citrate solution and spray-granulated. The temperature of spray granulation amounts to 40°–45°, the spraying time of the sodium citrate solution 6 minutes. Drying is then effected for 4 minutes. The sieved mannitol is subsequently placed into the bucket of the spray granulator and the whole material is thoroughly mixed. The corresponding amount of polyvinyl pyrrolidone is subsequently dissolved in 3000 cc of water, and the 2-(2-chlorophenyl)-3-(5-nitro-2-furyl) acrolein-guanyl hydrazone as well as the 6-chlorobenzisothiazolinone are suspended therein. The resulting suspension is again spray-granulated with the mixture in the spray granulator. Half of the above suspension is first sprayed into this mixture within 25 minutes, whereupon the apparatus is turned off and the precipitate on the wall of the granulator is scratched off. Spraying is subsequently continued for 25 minutes while adding the second half of the suspension. Rinsing out is then effected with 500 cc of water. The resulting product is then dried at the above temperature for 35 minutes, whereupon the temperature is increased to 60° and drying is terminated over a further 6 minutes. The resulting granulate is usually very fine-grained. It is rapidly sprayed with a total of 3 liters of water and then dried at 60°. Sifting is then effected with a DIN sieve No. 7.

EXAMPLE 29

Production of a tablet

| Composition of the tablet mixture: | |
|---|---|
| 6-chlorobenzisothiazolinone | 10 g |
| 2-(2-chlorophenyl)-3-(5-nitro-2-furyl) acrolein-guanyl hydrazone | 30 g |
| bismuth subcarbonate | 200 g |
| polyvinyl pyrrolidone | 20 g |
| mannitol | 240 g |
| Polyclar (higher molecular weight polyvinyl pyrrolidone) | 5 g |
| magnesium stearate | 5 g |
| total amount | 510 g |

The first five ingredients are spray-granulated in a granulator as described in Example 28. The resulting granulate is dried, whereupon the Polyclar and magnesium stearate are added to the resulting powder, the mixture is homogenized in a mixer and pressed into tablets in a press.

The 2-(2-chlorophenyl)-3-(5-nitro-2-furyl) acrolein-guanyl hydrazone is preferably used in hydrochloride salt form.

EXAMPLE 30

The compositions of Examples 27 to 29 may be reformulated using, in place of the 6-chlorobenzisothiazolinone, 6-bromo-, 6-methyl- or 6-methoxybenzisothiazolinone.

EXAMPLE 31

The compositions of Examples 27 to 30 may be reformulated using, in place of the 2-(2-chlorophenyl)-3-(5-nitro-2-furyl)acrolein-guanyl hydrazone, the compound of Example 21 or 22.

EXAMPLE 32

The compositions of Examples 27 to 30 may be reformulated using, in place of the 2-(2-chlorophenyl)-3-(5-nitro-2-furyl)acrolein-guanyl hydrazone, the compound of any one of Examples 1 to 19 and 23 to 26.

We claim:

1. A pharmaceutical composition useful in combatting fungi, bacteria or protozoa which comprises a first compound 6-chlorobenzisothiazolinone in free base or pharmaceutically acceptable acid addition salt form in combination with a second compound selected from the group consisting of 2-(2-chlorophenyl)-3-(5-nitro-2-furyl) acrolein guanylhydrazone, 2-(4-bromophenyl)-3-(5-nitro-2-furyl) acrolein guanylhydrazone, and 2-(4-chlorophenyl)-3-(5-nitro-2-furyl) acrolein guanylhydrazone, in free base or pharmaceutically acceptable acid addition salt form as the active ingredients said first compound being present in an amount of from 10 to 90% and said second compound being present in an amount of from 90 to 10% based on total weight of the active ingredients.

2. The pharmaceutical composition of claim 1 in which the first compound is 6-chlorobenzisothiazolinone, and the second compound is 2-(2-chlorophenyl)-3-(5-nitro-2-furyl) acrolein guanylhydrazone.

3. The pharmaceutical compositon of claim 1 in which the first compound is 6-chlorobenzisothiazolinone, and the second compound is 2-(4-bromophenyl)-3-(5-nitro-2-furyl) acrolein guanylhydrazone.

4. The pharmaceutical composition of claim 1 in which the first compound is 6-chlorobenzisothiazolinone, and the second compound is 2-(4-chlorophenyl)-3-(5-nitro-2-furyl) acrolein guanylhydrazone.

5. A method of combatting fungi, bacteria or protozoa in mammals comprising administering to a mammal in need of such treatment, an effective amount of a composition of claim 1.

6. The method according to claim 5, in which the bacteria is Staph. aureus, E. coli or Proteus vulgaris.

7. The method according to claim 5, in which the bacteria is Staph. aureus or E. coli.

* * * * *